United States Patent
Lee et al.

(10) Patent No.: US 10,254,251 B2
(45) Date of Patent: Apr. 9, 2019

(54) JOINING QUALITY DIAGNOSIS DEVICE OF PANEL ELEMENT

(71) Applicants: HYUNDAI MOTOR COMPANY, Seoul (KR); KIA MOTORS CORPORATION, Seoul (KR); IUCF-HYU (Industry-University Cooperation Foundation Hanyang University), Seoul (KR)

(72) Inventors: Jong Ho Lee, Seoul (KR); Yunsang Kwak, Uiwang-si (KR); Junhong Park, Seongnam-si (KR)

(73) Assignees: HYUNDAI MOTOR COMPANY, Seoul (KR); KIA MOTORS CORPORATION, Seoul (KR); IUCF-HYU (Industry-University Cooperation Foundation Hanyang University), Seoul (KR)

( * ) Notice: Subject to any disclaimer, the term of this patent is extended or adjusted under 35 U.S.C. 154(b) by 221 days.

(21) Appl. No.: 15/376,581

(22) Filed: Dec. 12, 2016

(65) Prior Publication Data
US 2018/0120263 A1   May 3, 2018

(30) Foreign Application Priority Data
Oct. 27, 2016   (KR) .................. 10-2016-0141391

(51) Int. Cl.
*G01N 29/12* (2006.01)
*G01N 3/20* (2006.01)
(Continued)

(52) U.S. Cl.
CPC .......... *G01N 29/12* (2013.01); *B23K 31/125* (2013.01); *G01N 3/20* (2013.01); *G01N 29/24* (2013.01);
(Continued)

(58) Field of Classification Search
CPC ...... G01N 29/12; G01N 29/24; G01N 29/348; G01N 29/4418; G01N 29/14; G01N 3/20; G01N 3/32
See application file for complete search history.

(56) References Cited

U.S. PATENT DOCUMENTS 4,188,830 A * 2/1980 Mason ............... G01N 3/38
  73/801
4,549,437 A * 10/1985 Weins ............... G01N 29/14
  73/587

(Continued)

FOREIGN PATENT DOCUMENTS

EP   2946869 A1   11/2015
JP   62-119453 A   5/1987
(Continued)

*Primary Examiner* — Helen C Kwok
(74) *Attorney, Agent, or Firm* — Knobbe Martens Olson & Bear LLP (57) ABSTRACT

A device for evaluating quality of welding spots of a panel is disclosed. The device includes a vibration transferring member, a first access member contacted with one surface of one end portion of the vibration transferring member and with the one surface of the panel, a second access member contacted with one surface of the other end portion of the vibration transferring member and with the one surface of the panel, an oscillator for supplying vibration to the one end portion of the vibration transferring member, a sensor disposed on the vibration transferring member to detect characteristic of vibration transferred along the vibration transferring member, and a computing device for analyzing characteristic of the welding spots using characteristic of vibration detected in the sensor.

12 Claims, 7 Drawing Sheets

(51) Int. Cl.
    *B23K 31/12*     (2006.01)
    *G01N 29/24*     (2006.01)
    *G01N 29/44*     (2006.01)
    *G01N 29/34*     (2006.01)
    *B23K 101/00*     (2006.01)

(52) U.S. Cl.
    CPC ....... *G01N 29/348* (2013.01); *G01N 29/4418* (2013.01); *B23K 2101/006* (2018.08); *G01N 2203/0282* (2013.01); *G01N 2203/0296* (2013.01); *G01N 2291/0234* (2013.01); *G01N 2291/0289* (2013.01); *G01N 2291/02827* (2013.01); *G01N 2291/2672* (2013.01)

(56) References Cited

U.S. PATENT DOCUMENTS

| | | | | |
|---|---|---|---|---|
| 4,901,575 | A * | 2/1990 | Bohannan | G01H 1/00 73/587 |
| 4,944,185 | A * | 7/1990 | Clark, Jr. | G01N 29/12 324/214 |
| 5,284,058 | A * | 2/1994 | Jones | G01N 3/32 73/579 |
| 6,234,022 | B1 * | 5/2001 | Tadokoro | G01M 7/025 73/593 |
| 6,236,143 | B1 * | 5/2001 | Lesieutre | H01L 41/0933 310/328 |
| 6,880,379 | B2 * | 4/2005 | Hedberg | G01N 3/30 702/38 |
| 6,880,403 | B1 * | 4/2005 | Shimada | G01M 7/00 73/600 |
| 7,332,849 | B2 * | 2/2008 | Ling | G01M 7/06 310/328 |
| 2010/0131114 | A1 * | 5/2010 | Stothers | F16F 7/1011 700/280 |
| 2015/0346232 | A1 * | 12/2015 | Pruksch | F16F 15/04 73/493 |

FOREIGN PATENT DOCUMENTS

| | | |
|---|---|---|
| JP | 4-40359 A | 2/1992 |
| JP | 4-265854 A | 9/1992 |
| JP | 6-50944 A | 2/1994 |
| JP | 6-118068 A | 4/1994 |
| JP | 9-171007 A | 6/1997 |
| JP | 2014-21018 A | 2/2014 |
| KR | 10-2015-0088896 A | 8/2015 |

\* cited by examiner

JOINING QUALITY DIAGNOSIS DEVICE OF PANEL ELEMENT

CROSS-REFERENCE TO RELATED APPLICATION

This application claims priority to and the benefit of Korean Patent Application No. 10-2016-0141391 filed in the Korean Intellectual Property Office on Oct. 27, 2016, the entire contents of which are incorporated herein by reference.

BACKGROUND (a) Field

The present disclosure relates to a joining quality diagnosis device of a panel element capable of diagnosing quality of a welding portion by transferring wave having a predetermined frequency to a predetermined area, analyzing the received wave being, and determining characteristic of a joined portion.

(b) Description of the Related Art

Welding processed components such as a door hood, which are comprised to a vehicle body, are manufactured by coupling a plurality of panels or parts with spot welding.

There is a method of projecting ultrasonic wave to a spot welding portion and then determining a diameter of a welding nugget based on the reflected wave thereof as a method for diagnosing quality of a welding portion of a welding processed component.

Further, there is a method of diagnosing quality of a welding portion by projecting sound wave to a spot welding portion and then analyzing the wave reflected from the welding portion.

In addition, a method of diagnosing quality of a welding portion by using an ultrasonic wave probe is also disclosed. Furthermore, there is a method of diagnosing quality of a welding portion by installing a transducer to a front end portion of an electrode of a spot welding machine and encoding elastic wave received from a welding portion.

Meanwhile, in the above mentioned approaches, accuracy may be deteriorated and it may be not easy that real binding force of a welding portion is diagnosed as quality of a welding processed component is determined through a frequency analyzing portion.

The disclosure of this section is to provide background of the invention. Applicant notes that this section may contain information available before this application. However, by providing this section, Applicant does not admit that any information contained in this section constitutes prior art.

SUMMARY

The present disclosure has been made in an effort to provide a joining quality diagnosis device of a panel element having advantages of reducing a time for measuring, improving availability for a user, and directly determining stiffness of a welded area with respect to measure stiffness of a predetermined area of a welded panel element by using vibration characteristic.

An aspect of the invention provides a system for testing a target object (metal member, panel) having a plurality of welding spots. The system scans the target object to determine bending stiffness at multiple locations of the target objects. The bending stiffness is a metric indicative of welding quality of welding spots formed in a corresponding portion of the target objects.

The system process bending stiffness at multiple locations to determine a portion or a location of the target objects where bending stiffness are relatively low compared to the other portions. When the system identifies a relatively low bending stiffness potentially indication a poor quality of spot welding, the system stores information that can identify a portion of the target object showing relatively low bending stiffness for further processing (additional spot welding).

Figure 1:
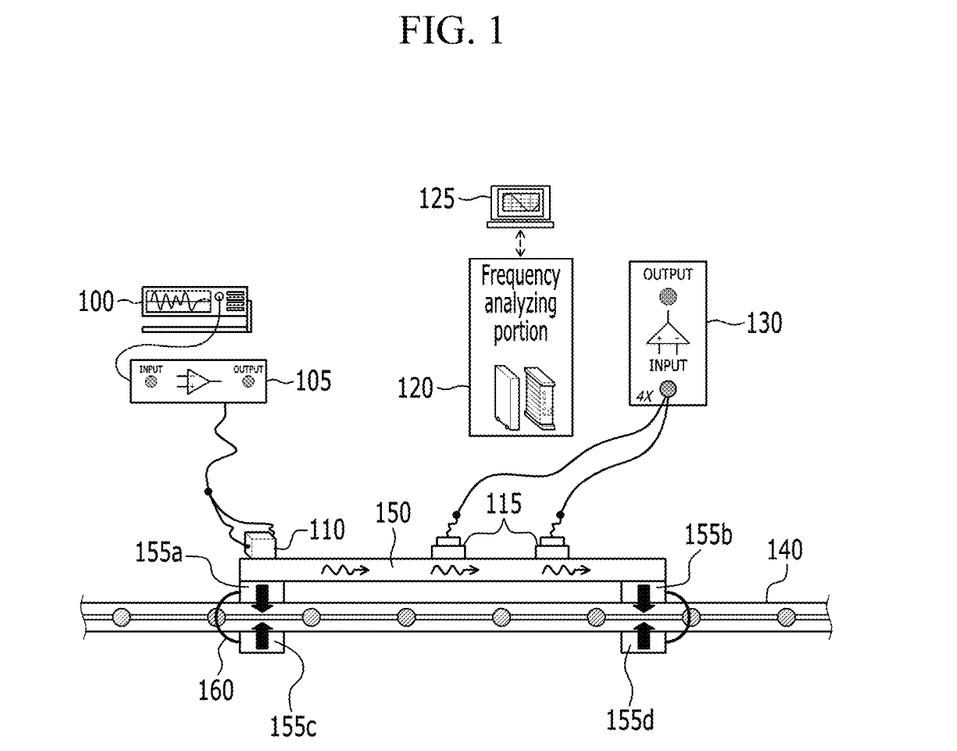
FIG. 1 is a schematic diagram of a joining quality diagnosis device of a panel element according to an embodiment of the present invention.
Figure 2:
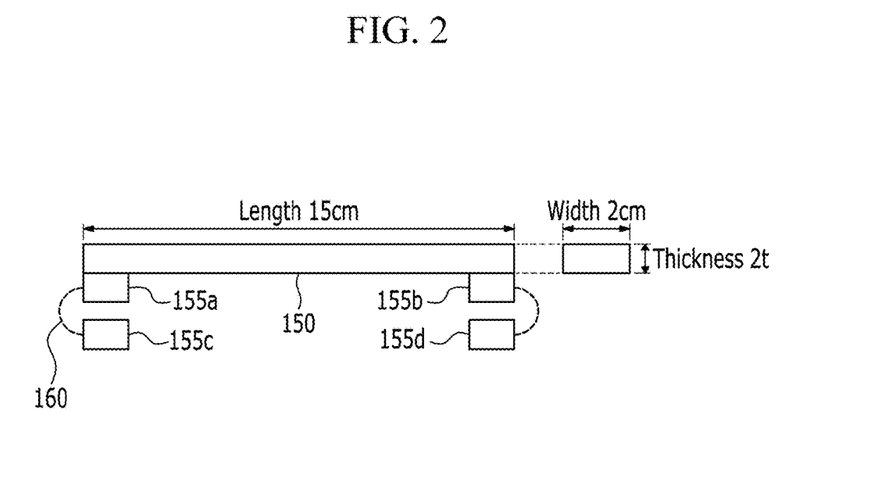
FIGS. 2, 3, 4, and 5 are schematic diagrams illustrating joining quality diagnosis devices of panel elements according to embodiments of the present invention.
Figure 3:
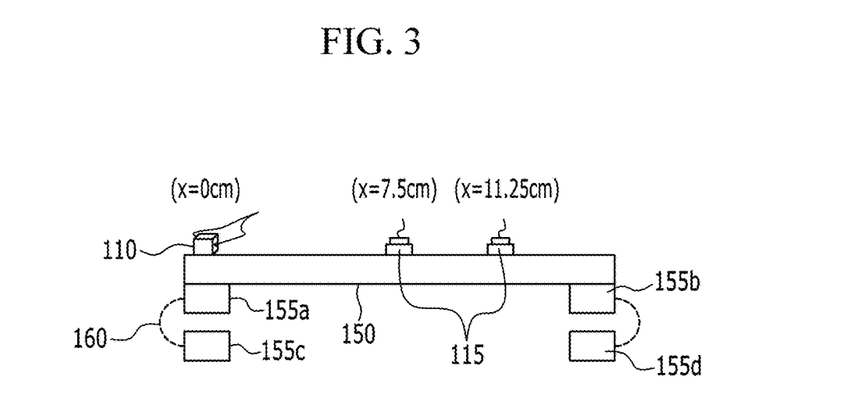
Figure 4:
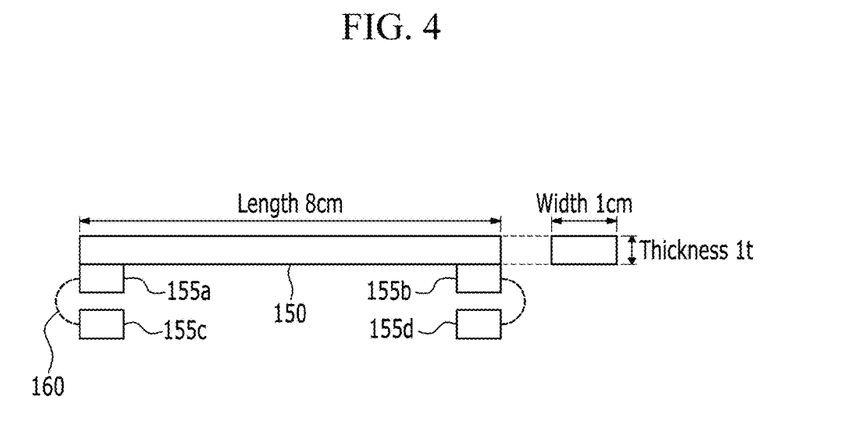
Figure 5:
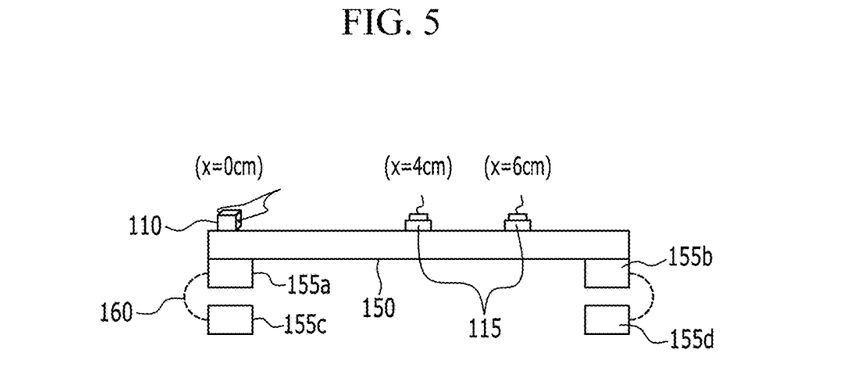

In embodiments, as illustrated in FIG. 1, a vibration transfer member 150 is displaced over a portion of a target object 140 including at least one welding spot (hatched circle in the target object 140). In embodiments, the vibration transfer member 150 is connected to the target object 140 using the connectors 115a, 115b while not directly contacting the target object 140. When the vibration member vibrates in response to operation of the vibrator 110, the vibrations is mechanically transmitted to the target object 140 via the connectors (155a, 155b, 155c, 155d). The sensors 115 captures signals representing vibration characteristics of the vibration member 150 and the corresponding portion of the target object 140 between two connectors (between 155a and 155b). Signals are processed to compute a metric representing quality of the welding spots (4 hatched circles between the connectors 155a, 155b). In embodiments, the vibrator 110 generates vibrations in a frequency within a range of 260 Hz and 340 Hz.

A joining quality diagnosis device of a panel element according to an embodiment of the present invention may be mounted to a panel element at which a welding portion is formed so as to diagnose join quality. The joining quality diagnosis device of a panel element may include a vibration transferring member disposed apart as a predetermined gap from one surface of the panel element, a first access member respectively contacted with one surface of one end portion of the vibration transferring member and the one surface of the panel element, a second access member respectively contacted with one surface of the other end portion of the vibration transferring member and the one surface of the panel element, an oscillator set so as to supply vibration having a predetermined frequency to the one end portion of the vibration transferring member, a sensor disposed apart as a predetermined distance from the oscillator and contacted with the vibration transferring member so as to detect characteristic of vibration moving along the vibration transferring member, and an analyzing portion analyzing characteristic of a predetermined area of the panel element corresponding with the vibration transferring member by analyzing vibration characteristic detected in the sensor.

The vibration transferring member may contain a steel material, and the join portion may have a portion which is spot-welded.

The first and second access members may be permanent magnets.

The first and second access members may be accessed to the one surface of the panel element, and the other surface of the panel element, and third and fourth access members may be disposed on respective positions corresponded with the first and second access members.

The joining quality diagnosis device may further include connecting wires connecting the first access member with the third access member and connecting the second access member with the fourth access member.

The sensors may be arranged with a predetermined gap in a length direction the vibration transferring member.

The sensor may be an acceleration sensor.

The vibration transferring member may contain an acryl material.

The analyzing portion may analyze a predetermined area of the panel element at which the vibration transferring member is disposed.

The joining quality diagnosis device may further include a display showing a data analyzed from the analyzing portion.

The vibration transferring member may be arranged side by side with the one surface of the panel element, and the characteristic of the predetermined area may be a bending stiffness of the panel element.

A diagnosis device, which is mounted on an exterior surface of a panel element so as to diagnose characteristic of the panel element, according to an embodiment of the present invention may include a vibration transferring member disposed apart as a predetermined gap from one surface of the panel element, a first access member respectively contacted with one surface of one end portion of the vibration transferring member and the one surface of the panel element, a second access member respectively contacted with one surface of the other end portion of the vibration transferring member and the one surface of the panel element, an oscillator set so as to supply vibration having a predetermined frequency to the vibration transferring member, and a sensor disposed apart as a predetermined distance from the oscillator and contacted with the vibration transferring member so as to detect characteristic of vibration moving along the vibration transferring member.

The diagnosis device may further include an analyzing portion analyzing characteristic of a predetermined area of the panel element corresponding with the vibration transferring member by analyzing vibration characteristic detected in the sensor.

The panel element may have a welding portion.

The analyzing portion may be set to analyze stiffness of the panel element.

<Description of symbols>

| | |
|---|---|
| 100: signal generator | 105: high voltage amplifier |
| 110: oscillator | 115: sensor |
| 120: frequency analyzing portion | |
| 125: display | |
| 130: input and output apparatus | |
| 140: panel element | |
| | 150: vibration transferring member |
| 155a: first access member | |
| 155b: second access member | |
| 155c: third access member | |
| 155d: fourth access member | |
| 155: access member | 160: connecting wire |

DETAILED DESCRIPTION OF THE EMBODIMENTS

Hereinafter, an embodiment of the present invention will be described in detail with reference to the accompanying drawings.

Merely, the size and thickness of each component illustrated in the drawings are arbitrarily shown for better understanding and ease of description, but embodiments of the present invention are not limited thereto. Thicknesses are enlarged to clearly express various portions and areas.

The drawings and description are to be regarded as illustrative in nature and not restrictive, and like reference numerals designate like elements throughout the specification.

In the following description, dividing names of components into first, second and the like is to divide the names because the names of the components are the same as each other and an order thereof is not particularly limited.

FIG. 1 is a schematic diagram of a joining quality diagnosis device of a panel element according to an embodiment of the present invention.

Referring to FIG. 1, a joining quality diagnosis device of a panel element includes, as constituent elements, a panel element 140, a welding portion, a signal generator 100, a high voltage amplifier 105, an oscillator 110, a vibration transferring member 150, a sensor 115, a first, second, third, and fourth access members 155a, 155b, 155c, and 155d, a connecting wire 160, an input and output apparatus 130, a frequency analyzing portion 120, and a display 125.

The signal generator 100 generates a predetermined frequency signal, and the high voltage amplifier 105 amplifies the generated frequency signal and then transfers the amplified signal to the oscillator 110.

In detail, the panel element 140 has a structure that two panels spot-joined through the welding portion, and the welding portions are arranged with a predetermined gap between two panels.

The vibration transferring member 150 is disposed apart as a predetermined gap from one surface of the panel element 140, and the first access member 155a is interposed between one end portion of the vibration transferring member 150 and the panel element 140, and the second access member 155b is interposed between the other end portion of the vibration transferring member 150 and the panel element 140.

The third access member 155c is mounted on the other surface of the first access member 155a, and the fourth access member 155d is mounted on the other surface of the second access member 155b. In addition, the one connecting wire 160 connects the first access member 155a and the third access member 155c, and the other one connecting wire 160 connects the second access member 155b and the fourth access member 155d.

The first and second access members 155a and 155b may be fixed to the vibration transferring member 150, and the first, second, third, and fourth access members 155a, 155b, 155c, and 155d may be made of permanent magnets adhering to the panel element 140.

FIGS. 2, 3, 4, and 5 are schematic diagrams illustrating joining quality diagnosis devices of panel elements according to embodiments of the present invention.

Referring to FIGS. 2 to 5, a length, a thickness, and a width of the vibration transferring member 150 may be varied depending on a design, and sizes, thicknesses, and lengths of the first, second, third, and fourth access members 155a, 155b, 155c, and 155d may be also varied depending on a design, and the connecting wire 160 may be made of a conductive material or a sub-conductive material as an elastic member.

Four spot welding portions (welding spots) may be formed to correspond with the vibration transferring member 150, and the number of welding portions and a gap therebetween may be varied according to an embodiment.

Further, the third and fourth access members 155c and 155d may be not provided, and the first and second access members 155a and 155b may be made of permanent magnets and may selectively contain rubber, plastic and metal materials or nonmetal material.

In addition, the sensor 115 may be an acceleration sensor, and the sensors 115 may be arranged with a predetermined distance in a length direction or a width direction of the vibration transferring member 150.

Furthermore, the first and second access members 155a and 155b may be formed along an appearance of the panel element 140 such that an access area is uniformly maintained.

Figure 6:
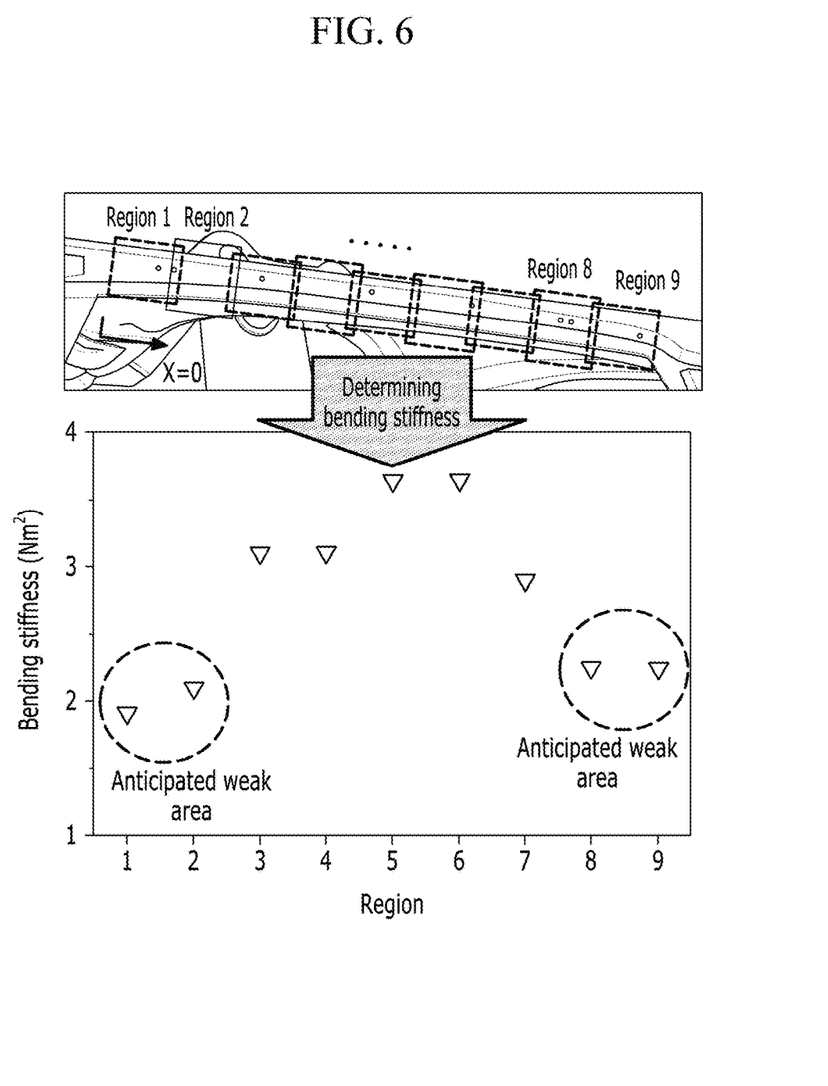
FIGS. 6, 7, and 8 are graphs representing analysis results a joining quality diagnosis device of a panel element according to an embodiment of the present invention.
Figure 7:
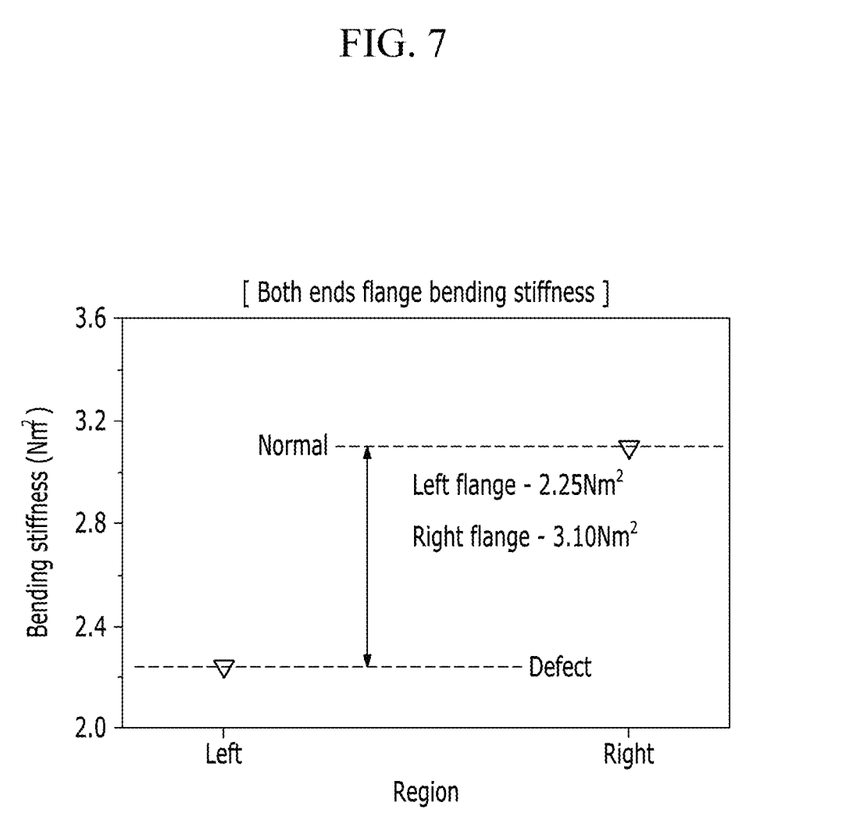
Figure 8:
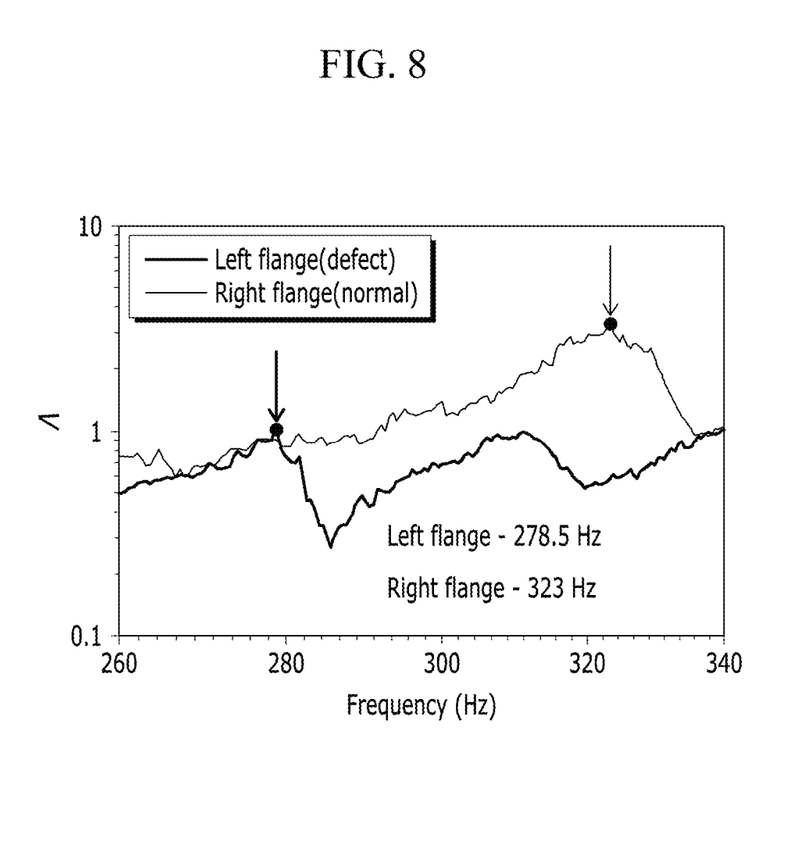

FIGS. 6, 7, and 8 are graphs representing analysis results a joining quality diagnosis device of a panel element according to an embodiment of the present invention.

Referring to FIG. 6, a horizontal axis represents respective diagnosed areas and a vertical axis represents a bending stiffness.

The analyzing portion 120 may determine a bending stiffness about respective areas by analyzing a vibration data.

As shown in FIG. 6, bending stiffness of a first area, a second area, an eighth area, and a ninth area are relatively low and bending stiffness of third, fourth, fifth, sixth, and seventh areas are relatively high.

Therefore, it may be determined that joining quality of welding portions of first, second, eighth, and ninth areas are relatively bad.

Referring to FIG. 7, a horizontal axis represents a position of the panel element 140 and a vertical axis represents a bending stiffness.

As shown in FIG. 7, bending stiffness to be lower than 2.4 are represented at a left side and bending stiffness to be 3.2 are represented at a right side. That is, bending stiffness of a left side having defect are low.

Referring to FIG. 8, a horizontal axis represents frequency being transferred from the oscillator 110 to the vibration transferring member 150 through the vibration transferring member 150, and a vertical axis represents characteristic of frequency being transferred to the sensor 115 along the vibration transferring member 150 mounted on the panel element 140.

As shown in FIG. 8, characteristic of frequency being transferred to the sensor 115 are different between a left flange having defect and a right flange to be normal.

Frequency characteristic is low at the left flange having defect in comparison with the right flange to be normal. In this regard, the characteristic is represented in case that excitation frequency is in a range about 120 Hz to 335 Hz.

Figure 9:
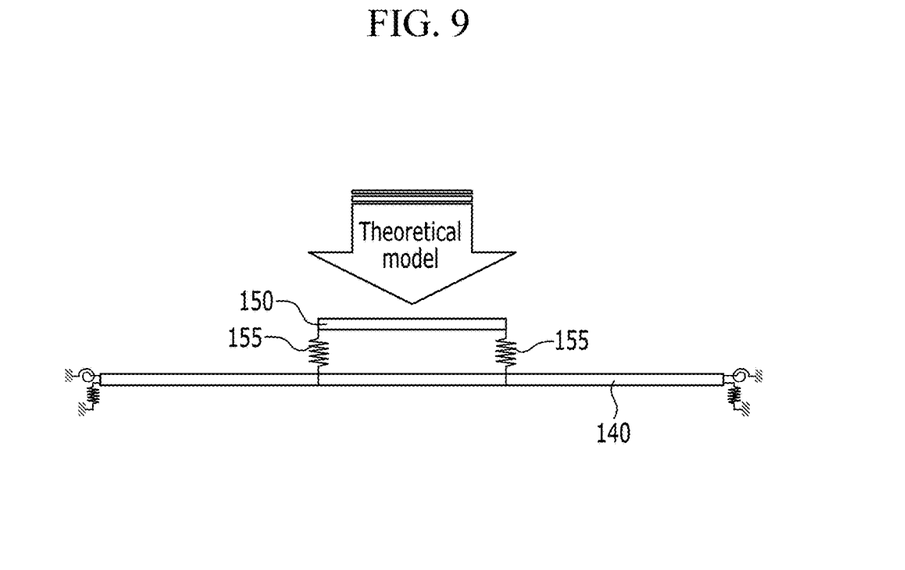
FIG. 9 is a schematic diagram illustrating a theoretical model of a joining quality diagnosis device of a panel element according to an embodiment of the present invention.

FIG. 9 is a schematic diagram illustrating a theoretical model of a joining quality diagnosis device of a panel element according to an embodiment of the present invention.

Referring to FIG. 9, on a state of supposing the welding area to equivalent beam element, a theoretical model of a structure that the vibration transferring member 150 is mounted on the welding area, which will be measured, through the access members 155a, 155b, 155c, and 155d is composed.

In addition, a bending stiffness may be anticipated by directly or indirectly comparing real generated frequency value with a result value calculated by using the theoretical model.

While this invention has been described in connection with its embodiments, it is to be understood that the invention is not limited to the disclosed embodiments, but, on the contrary, is intended to cover various modifications and equivalent arrangements.

What is claimed is:

1. A joining quality diagnosis device of a panel element mounted to the panel element where a welding portion is formed so as to diagnose join quality, comprising:
   a vibration transferring member disposed apart from one surface of the panel element with a predetermined gap;
   a first permanent magnet respectively contacted with one surface of one end portion of the vibration transferring member and the one surface of the panel element;
   a second permanent magnet respectively contacted with one surface of the other end portion of the vibration transferring member and the one surface of the panel element;
   an oscillator configured to supply vibration having a predetermined frequency to the one end portion of the vibration transferring member;
   a sensor disposed a predetermined distance from the oscillator and contacted with the vibration transferring member so as to detect characteristic of vibration along the vibration transferring member; and
   an analyzing portion configured to analyze characteristic of a predetermined area of the panel element corresponding to the vibration transferring member by analyzing the characteristic of vibration detected by the sensor, wherein:
   the vibration transferring member contains a steel material, and the welding portion is spot-welded,
   the first and second permanent magnets are in contact with the one surface of the panel element, and third and fourth permanent magnets are disposed at respective positions on an opposite surface of the panel element corresponding to the first and second permanent magnets, respectively,
   wherein the joining quality diagnosis device further comprises a first connecting wire connecting the first permanent magnet and the third permanent magnet, and a second connecting wire connecting the second permanent magnet and the fourth permanent magnet.

2. The joining quality diagnosis device of claim 1, further comprising sensors arranged along a length direction of the vibration transferring member with a predetermined gap between the sensors.

3. The joining quality diagnosis device of claim 1, wherein the sensor is an acceleration sensor.

4. The joining quality diagnosis device of claim 1, wherein the vibration transferring member contains an acrylic material.

5. The joining quality diagnosis device of claim 1, wherein the analyzing portion is configured to analyze the predetermined area of the panel element where the vibration transferring member is disposed.

6. The joining quality diagnosis device of claim 5, further comprising:
   a display configured to show data analyzed from the analyzing portion.

7. The joining quality diagnosis device of claim 5, wherein the vibration transferring member is arranged side by side with the one surface of the panel element, and the characteristic of the predetermined area indicates a bending stiffness of the panel element.

8. The joining quality diagnosis device of claim 1, wherein the panel element comprises two panels joined through welding portions.

9. A diagnosis device mounted on an exterior surface of a panel element so as to diagnose characteristic of the panel element, comprising:
- a vibration transferring member disposed apart from one surface of the panel element with a predetermined gap;
- a first permanent magnet respectively contacted with one surface of one end portion of the vibration transferring member and the one surface of the panel element;
- a second permanent magnet respectively contacted with one surface of the other end portion of the vibration transferring member and the one surface of the panel element;
- an oscillator configured to supply vibration having a predetermined frequency to the vibration transferring member; and
- a sensor disposed a predetermined distance from the oscillator and contacted with the vibration transferring member so as to detect characteristic of vibration along the vibration transferring member, wherein:
- the vibration transferring member contains a steel material, and the diagnosis device further comprises a welding portion that is spot-welded,
- the first and second permanent magnets are in contact with the one surface of the panel element, and third and fourth permanent magnets are disposed at respective positions on an opposite surface of the panel element corresponding to the first and second permanent magnets, respectively,
- wherein the diagnosis device further comprises a first connecting wire connecting the first permanent magnet and the third permanent magnet, and a second connecting wire connecting the second permanent magnet and the fourth permanent magnet.

10. The diagnosis device of claim 9, further comprising:
an analyzing portion configured to analyze characteristic of a predetermined area of the panel element corresponding to the vibration transferring member by analyzing the characteristic of vibration detected by the sensor.

11. The diagnosis device of claim 9, wherein the panel element comprises the welding portion.

12. The diagnosis device of claim 10, wherein the analyzing portion is configured to analyze stiffness of the panel element.

* * * * *